United States Patent
Jat (12)

(10) Patent No.: US 6,399,384 B1
(45) Date of Patent: Jun. 4, 2002

(54) CONDITIONAL IMMORTALIZATION OF CELLS

(75) Inventor: Parmjit Jat, London (GB)

(73) Assignees: Reneuron Limited; Ludwig Institute for Cancer Research, both of (GB)

( * ) Notice: Subject to any disclaimer, the term of this patent is extended or adjusted under 35 U.S.C. 154(b) by 0 days.

(21) Appl. No.: 09/663,537

(22) Filed: Sep. 15, 2000

(51) Int. Cl.⁷ .............................................. C12N 15/867
(52) U.S. Cl. ...................... 435/456; 435/368; 536/23.5
(58) Field of Search ................................. 435/366, 368, 435/456; 424/93.7; 536/23.5

(56) References Cited

U.S. PATENT DOCUMENTS

| | | | | |
|---|---|---|---|---|
| 5,270,191 A | * | 12/1993 | Mckay et al. | ............ 435/172.3 |
| 6,166,178 A | * | 12/2000 | Cech et al. | |

FOREIGN PATENT DOCUMENTS

| | | |
|---|---|---|
| GB | 2317891 | 4/1998 |
| WO | 9416059 | 7/1994 |
| WO | 9619580 | 12/1995 |
| WO | 9710329 | 9/1996 |
| WO | 9837181 | 2/1998 |

OTHER PUBLICATIONS

Mark F. Mehler et al, Progenitor Cell Biology, Implications for Neural Regeneration, Section Editor: David E. Pleasure, MD Arch Neurol/vol. 56, Jul. 1999.*

Kiyono, Tohru, Scott A. Foster, Jenn I. Koop et al. (Nov. 5, 1998) "Both Rb/p16$^{INK4a}$ inactivation and telomerase activity are required to immortalize human epithelial cells" *Nature* 396:84–88.

Stamps, Alasdair C., susan C. Davies, Jacqueline Burman and Michael J. O'Hare (1994) "Analysis Of Proviral Integration In Human Mammary Epithelial Cell Lines Immortalized By Retroviral Infection With A Temperature–Sensitive SV40 T–Antigen Construct" *Int. J. Cancer* 57:865–874.

Hahn, William C., Christopher M. Counter, Ante S. Lundberg et al. (Jul. 29, 1999) "Creation of human tumour cells with defined genetic elements" *Nature* 400:464–468.

Zhu, Jiyue, He Wang, J. Michael Bishop and Elizabeth H. Blackburn (Mar. 1999) "Telomerase extends the lifespan of virus–transformed human cells without net telomere lengthening" *Proc. Natl. Acad. Sci. USA* 96:3723–3728.

Bodnar, Andrea G., Michel Quellette, Maria Frolkis et al. (Jan. 1998) "Extension of Life–Span by Introduction of Telomerase into Normal Human Cells" *Science* 279:349–252.

Counter, Christopher M. et al. (Dec. 1998) "Dissociation among in vitro telomerase activity, telomere maintenance, and cellular immortalization" *PNAS* (USA) 95(25):14723–14728.

Reynolds, Brent A. and Samuel Weiss (Mar. 1992) "Generation of Neurons and Astrocytes from Isolated Cells of the Adult Mammalian Central Nervous System" *Science* 255:1707–1710.

U.S. application No. 09/537,617, Hodges, filed Mar. 29, 2000.*

U.S. application No. 09/672,606, Sinden et al., filed Sep. 28, 2000.*

U.S. application No. 09/760,274, Sinden et al., filed Jan. 12, 2001.*

U.S. application No. 09/696,569, Price et al., Oct. 25, 2000.*

\* cited by examiner

*Primary Examiner*—James Ketter
(74) *Attorney, Agent, or Firm*—Saliwanchik, Lloyd & Saliwanchik

(57) ABSTRACT

A recombinant, or genetically engineered, mammalian cell, comprises a conditionally-inducible oncogene and an exogenous polynucleotide encoding the catalytic sub-unit of the telomerase complex. The recombinant cells are useful in therapy, to replace lost or damaged cells.

14 Claims, 1 Drawing Sheet

CONDITIONAL IMMORTALIZATION OF CELLS

FIELD OF THE INVENTION

The present invention relates to the immortalisation of mammalian cells for therapeutic application.

BACKGROUND TO THE INVENTION

There is a growing awareness and understanding of the importance of transplantation therapy to treat damage to tissues and organs. While organ transplantation is widely practiced, therapies based on the transplantation of individual cells are still in a relatively early phase of clinical development.

For example, there is growing recognition that the transplantation of suitable cells into a damaged brain may improve or correct any sensory, motor, behavioural or psychological deficits caused by the damage.

For cell-based therapies to be useful, it must be possible to obtain sufficient cells for transplantation. One means for ensuring this is to culture undifferentiated cells under conditions which allow repeated cell division and growth. One difficulty with using undifferentiated cells is that unregulated cell division must be switched off either prior to or on transplantation into the patient, to prevent uncontrolled growth at the site of transplantation.

Many different techniques have been developed to provide suitable cells for transplantation. With regard to neural transplantation, one approach has been to maintain undifferentiated foetal cells under culture conditions that permit cell division to occur, and to subsequently induce differentiation in vitro, prior to transplantation.

Reynolds and Weiss, Science, 1992;255:1707, disclose the use of epidermal growth factor (EGF) to induce the in vitro proliferation of adult mouse brain cells. Under suitable conditions it was thought that the cells could be induced to differentiate into astrocytes and neurons.

International Patent Application No. WO-A-94/16059 discloses a technique for maintaining a primary neuronal cell culture in vitro by culturing the cells in a serum-free media supplemented with at least one trophic factor.

International Patent Application No. WO-A-97/10329 discloses an alternative technique, using a conditionally-immortalised cell line. This cell line comprises an immortalising temperature-sensitive oncogene which, under permissive conditions, maintains neuroepithelial stem cells in the undifferentiated state. Upon transplantation the oncogene is switched off due to the higher temperature of the human body (37° C.) and the cells differentiate into the cell types required to repair damage. The advantage of using the oncogene is that the cells are maintained in the undifferentiated state until transplantation, at which point the cells differentiate, in response to the specific damage, into the phenotype of the damaged or lost cells. U.S. Pat. No. 5,688,692 also discloses cells expressing a non-DNA binding, temperature-sensitive T antigen.

However, it is recognised that although human cells expressing oncogenes can have an extended life, they still stop dividing and eventually undergo crisis (cell death).

It has also been proposed that human cells can be immortalised by reconstituting telomerase activity BY incorporating an exogenous copy of the catalytic subunit of human telomerase (Bodnar et al, Science, 1998; 279:249–252). Telomerase acts to maintain telomerase found at the ends of chromosomes, and it is believed that the gradual shortening of telomeres during cell duplication contributes to senescence and that therefore reconstituting telomerase immortalises cells. Human telomerase has now been used to immortalise many different cell types.

Counter et al., PNAS (USA), 1998; 95(25):4723–14728, also discloses that ectopic expression of the telomerase catalytic subunit (hTERT) can allow post senescent cells to proliferate beyond crisis to cellular immortality. The cells studied were transformed with an oncogene expressing SV40 T-antigen. However, the authors conclude that hTERT expression alone may suffice to immortalise cells, and that activation of hTERT may be a critical step in tumour progression. Therefore, the general teaching of this publication is that hTERT transformed cells would be immortal. This means that the cells would be unsuitable for use in transplantation therapy.

Therefore, while many of the techniques disclosed above may be useful, there is still a need for methods to obtain cells which retain immortality prior to transplantation, but which lose immortality on transplantation.

SUMMARY OF THE INVENTION

The present invention is based on the realisation that cells transduced with a conditionally-inducible oncogene and at least the catalytic subunit of the telomerase complex are immortal under permissive conditions but lose immortality under non-permissive conditions.

According to one aspect of the present invention, a recombinant, or genetically engineered, mammalian cell comprises a conditionally-inducible or temperature-sensitive oncogene, and an exogenous polynucleotide encoding at least the catalytic sub-unit of the telomerase complex.

According to a second aspect of the invention, a recombinant polynucleotide construct comprises a gene that encodes at least the catalytic sub-unit of the telomerase complex, and a conditionally-inducible or temperature-sensitive oncogene.

According to a third aspect, a method for immortalising a mammalian cell comprises incorporating, within a proliferating mammalian cell, a conditionally-inducible oncogene and an exogenous polynucleotide encoding the catalytic sub-unit of the telomerase gene.

According to a fourth aspect, the cells of the present invention may be used in therapy, in particular in the manufacture of a medicament for the treatment of a disease associated with cell loss or damage. For example, neuroepithelial stem cells may be used for the treatment of disorders associated with brain damage e.g. Alzheimers.

It has been found that cells according to the present invention retain a high level of stability and at non-permissive temperatures are not immortal.

This is a surprising and important finding as it would be expected, based on the prior art, for the cells to remain immortal, due to the reconstitution of the telomerase activity. However, it appears that, although the gene encoding the telomerase is constitutive, the telomerase does not act to retain immortality. The retention of conditionality and increased stability, makes the cells of the present invention suitable to be passaged serially to derive a cell line for transplantation.

DESCRIPTION OF THE DRAWINGS

The following figures illustrate the invention.

DESCRIPTION OF THE INVENTION

Figure 1:
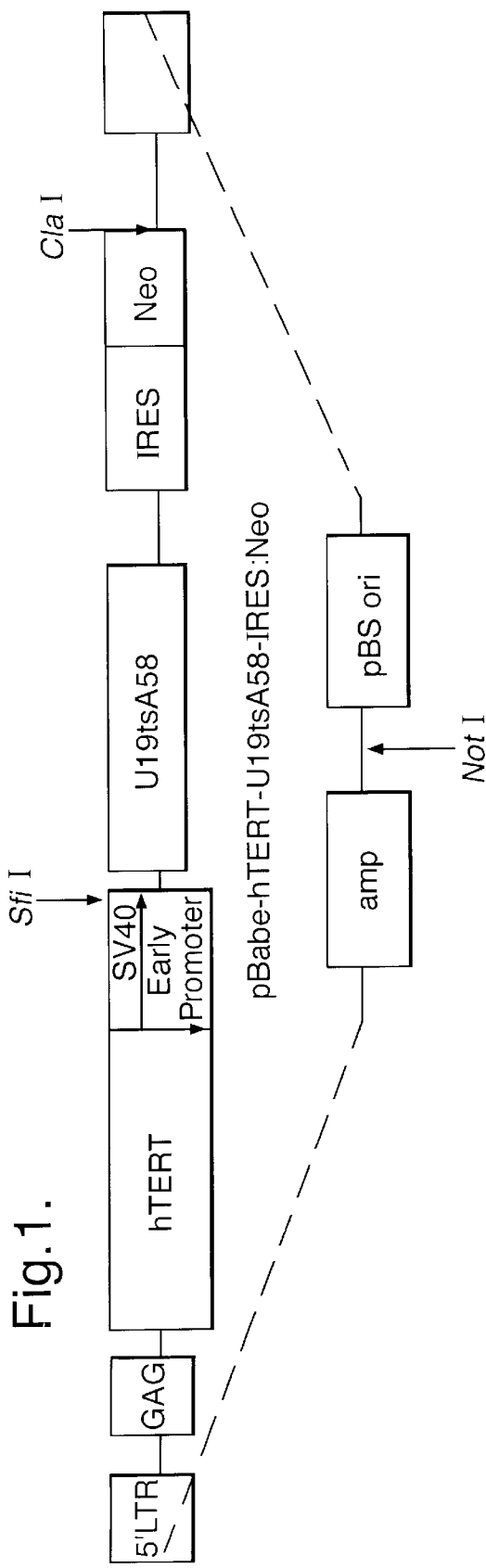
FIG. 1 is a schematic illustration of a polynucleotide construct containing both the hTERT and the temperature-sensitive oncogene encoding the SV40 large T-antigen.

The present invention discloses methods for preparing cells which are suitable for transplantation therapy and which are immortal up to the time of transplantation.

The cells require a conditionally-inducible oncogene to be present. The term "conditionally-inducible" is used herein to refer to oncogenes, the expression of which can be regulated under certain conditions. The oncogene will undergo expression when so-called permissive conditions are applied. For example, some oncogenes are temperature-sensitive and are only expressed when the temperature of their environment is below a certain value. In one embodiment of the invention, the oncogene that is used is a non-DNA binding, temperature-sensitive, mutant of the SV-40 large T-antigen gene (U19tsA58). Suitable alternatives are also known and include the oncogene of the polyoma T-antigen.

The cells also require an exogenous polynucleotide that encodes at least the catalytic sub-unit of the telomerase complex. The term "exogenous" is used herein in its normal context to refer to the polynucleotide introduced into the cell, and distinguish from naturally-occurring endogenous polynucleotides. The catalytic sub-unit of the telomerase complex is an enzyme that acts like a reverse transcriptase, and is known in the art. The human sub-unit is disclosed in GB-A-2317891.

The oncogene and the polynucleotide encoding the telomerase may be comprised in a recombinant DNA or retroviral vector or construct to transduce/infect the cells. The two components may be incorporated into one vector or each may be comprised in a separate vector. The vectors or constructs of the invention may further comprise a suitable promoter region to initiate transcription of DNA and a selectable marker which may be used to identify those cells that have undergone transduction/infection. Regulation of expression may be carried out by methods known to the skilled person. For example, regulation may be effected using the long terminal repeat (LTR) promoter. Alternative promoters will be apparent to the skilled person. For example, regulation may be effected using the cytomegalovirus (CMV) promoter. The CMV promoter is a very strong promoter, and may be preferred when the cells are neural cells, e.g. neuroepithelial stem cells.

Methods for introducing suitable constructs into cells, are known to the skilled person.

Any mammalian cell may be used in the present invention.

For example, the cell may be an endothelial cells, and may be used for the revascularisation of the leg, heart and other organs. Preferably, the cell is a human somatic cell, e.g. human epithelial stem cell, which is capable of differentiation into a specific cell type. A particularly preferred cell is a human neuroepithelial stem cell which may be used in neural transplantation to repair cell loss or damage and correct behavioural or psychological deficits. Alternatively, the cell may be a differentiated cell, e.g. the β cells of Islets of Langerhans. Additional cells may include but are not limited to those obtainable from the endocrine glands, retinal cells, cochlear cells, liver cells, osteoblast and osteoclasts, myoblasts and keratinocytes.

Preferably, the oncogene and the telomerase are incorporated into the cell during the early culture phase, usually within the first 10 cell divisions. The order of incorporating the oncogene and telomerase is not critical to the success of the method, although it is preferred that the telomerase is introduced first. This is because it has been found, surprisingly, that introducing the telomerase first provides better assurance for achieving a dipoid cell line.

The transduced or infected cells may be cultured under conditions known to those skilled in the art. It is preferable that the cells are cultured under non-stressed conditions. A skilled person will appreciate the conditions suitable for each particular cell type, based on conventional culture techniques.

The invention will now be described further in the following Examples with reference to the drawings. The Examples show that by transducing suitable human cells with a temperature-sensitive oncogene and the catalytic sub-unit of the telomerase complex, it is possible to retain stability as the cell cultures are passaged in a suitable culture medium.

EXAMPLE 1

1. Isolation of mammary interlobular fibroblasts (HMF) and mammary microvascular endothelial (MMVE) cells:

Cultures of mammary interlobular fibroblasts and mammary microvascular endothelial cells were prepared from normal breast tissue, obtained with consent from patients undergoing cosmetic surgery (reduction mammoplasty). Cultures of interlobular fibroblasts were prepared as described in Atherton et al, J. Cell Sci., 107:2931–2939, and maintained with Dulbecco's Modified Eagles medium (DMEM) supplemented with 10% fetal calf serum and antibiotics (penicillin-streptomycin). Endothelial cells from microvessels were isolated by immunomagnetic sorting of primary cultures, using the QBEND-40 mouse monoclonal antibody against thrombomodulin, essentially as described by Drake & Lock, Human Reprod., 1992; 6:1156–1159. Endothelial cultures were established and maintained in EGM-2 medium (Biowhittaker).

2. In vitro culture of cells to senescence.

As a control, preparation of cells were cultured to determine the point of senescence. The cells were found to have a culture lifespan of between 5–7 passages at a split ratio of 1:4 when cultured in EGM-2. Apart from an accumulation of granular particles in the cytoplasm, the senescent cells otherwise resembled their early-passage counterparts, differing only in the complete absence of mitosis.

3. Transduction of tsA58-U19 and extended growth to crisis.

Cell preparations from different individual donors were transduced, while still proliferating at passages 3–4, with the tsA58-U19 (Almazan and McKay, Brain Res., 1992; 579 (s) :234–245) double recombinant mutant of the SV40 T-antigen gene in the pZIP vector containing the neo-r gene. Transduction was carried out using a helper virus-free amphotropic retroviral packaging system (PA317, Clone 8) as described in Stamps et al., Int. J. Cancer, 1994; 57(6):865–874. Polybrene at 8ug/ml was used as an adjuvant to improve virus uptake.

Transduction frequencies varied between 10–25% after selection with geneticin at 0.25 mg/ml. After transfer to the permissive temperature for tsA58 (33.5° C.) these cultures were passaged for between 15 and 25 further passages at a split ratio of 1:4. During this time all cells remained stringently temperature-sensitive with little or no growth at 36.5° C. and above. In all cases, however, growth eventually ceased with the appearance of abnormal mitosis and abnormal cell morphologies including size and nuclear heterogeneity, indicative of crisis. A total of not less than $10^8$ cells in total have been passaged to crisis, without a single instance of 'spontaneous' immortalisation being observed. This is in contrast to mammary epithelial cells, which repeatedly immortalise at a frequency of approximately 1 in $5\times10^6$ cells maintained to crisis.

4. Transduction to h-TERT and subsequent immortalisation with retention of conditional growth.

Early-passaged cells from one donor transduced with the ts T antigen system (MMVE-2) were further transduced with the full-length cDNA copy of the catalytic sub-unit of the human telomerase gene in the pBabe vector (Morgenstern and Land, Nucleic Acids Research, 1990; 18:3587–3596) together with a hygromycin B-resistance gene, using a human amphotropic packaging system (TE-FLY). A series of four cloned packaging lines were used, having been selected previously for highest titres on the basis of transfer of hygromycin resistance to a target human cell line (EJ bladder carcinoma cells). Each was used to transduce, in duplicate, the MMVE-2 ts T cells in the presence of 8 μg/ml polybrene. Successful transduction was observed after selection 25 μg/ml hygromycin B.

Surprisingly, the transduced cells appeared to overcome senescence, and continued to proliferate at 33.5° C., without any overt crisis or change in proliferation rates, for over 40 weeks. The cells have so far undergone >100 population doublings at a constant rate, and appear to be functionally immortal.

When tested for temperature sensitivity by replicate culture at 33.5, 36.5 and 39.5° C., the hTERT transduced MMVE-2 tsT cells were, surprisingly, as sensitive as early passaged tsT only cells. Contrary to what might be expected, there was little growth at 36.5° C. and none at 39.5° C., i.e. the cells were conditionally immortal. All cultures were carried out with the EGM-2 medium which contains a variety of endothelial-specific growth factors, including b-FGF, VEGF, IGF-2 and heparin, as well as 2% FCS, thus avoiding the testing of cells under sub-optimal or 'stressed' growth conditions.

To determine the extent to which temperature-induced growth arrest was irreversible, the fibroblast cultures were analysed using a clonogenic assay in which the colony forming efficiency (CE) was determined under optimal conditions (5% oxygen at 33.5° C.), after different periods of growth arrest at 39.5° C. There was a substantial reduction in CE in most cultures which was proportional to the time at the non-permissive temperature. In one of the HMF cultures, for example, the CE after 14 days at 39.5° C. had dropped to <5% of control value, with most colonies being small and abortive. The results demonstrate the progressive irreversibility of the transduced cells and show that this is due to the thermal inactivation of T-antigen rather than a non-specific effect of heat shock.

The cells were also tested to establish whether they undergo biochemical senescence upon inactivation of T antigen, by staining cultures for senescence-activated acid β-galactosidase. After 4–8 days at 39.5° C. all the fibroblast cultures showed varying numbers of positive cells (1–10%), whereas no positive cells were detected in corresponding cultures at 33.5° C. (<0.1%). This compares with a crisis culture of T-antigen only HMF fibroblasts where 53% of the cells were positive. This demonstrates that the immortalised cells are dependent upon T-antigen to maintain growth, and that inactivation of T-antigen causes irreversible cessation of cell growth, and entry into senescence.

The cell cultures were also karyotyped to determine whether the order and timing of retroviral gene transduction affected the chromosomal status of the resulting cells. A diploid or near-diploid modal number of chromosomes (46) was observed in both MMVE and HMF cells; derived by introducing both genes during the early phase (i.e. within the first 10 passages) with hTERT first. When both genes were introduced during the early phase with the oncogene first, the cells were shown to have a bimodal karyotype with near diploid and near tetraploid modes. This is a surprising finding and demonstrates that diploid cells can be prepared more effectively by choosing to insert the catalytic subunit of telomerase first into the cell.

In summary, the results obtained show, surprising, that cells comprising the full-length gene encoding the telomerase catalytic sub-unit and the temperature-sensitive oncogene, remain conditional for growth, i.e. the cells are not immortal at high temperature.

The above results demonstrate that separate transduction with a temperature-sensitive oncogene and a catalytic telomerase subunit, can exhibit improved characteristics compared to cells comprising only the temperature-sensitive oncogene.

Although separate transduction shows good results, it may be easier to construct a suitable vector having both the oncogene and the gene encoding the telomerase.

EXAMPLE 2

This Example demonstrates the production of suitable expression vectors co-expressing thermolabile T-antigen derived from the non-DNA binding mutant of the SV40 early region (U19tsA58); the catalytic sub-unit hTERT of the telomerase complex (cDNA) (Counter et al., PNAS, 1998; 95 (25):14723–14728); and a dominantly-acting selectable neomycin phosphotransferase resistant marker (Neo) which encodes resistance to G418 (Clontech). The final construct was assembled in the high titre Moloney murine leukaemia virus (Mo MuLV) based retroviral expression vector, pBabe (Morgenstern and Land, Supra). The retrovirus lifecycle was used to convert the SV40 early region into viruses that make only the large T antigen. All constructs were assembled in a rec A-host (JS4-rec A-derivative of MCl061) using ampicillin selection.

Two Versions of the vector were constructed:

Construct 1

This construct is illustrated in FIG. 1. Mo MuLV LTR was used to drive hTERT, and the SV40 early promoter is used to drive both U19tsA58 and Neo. An internal ribosome entry site (IRES) was integrated between the U19tsA58 and Neo genes (fused in frame to the Neo gene) to induce reinitiation of translation by eukaryotic ribosomes.

Construct 2

Figure 2:
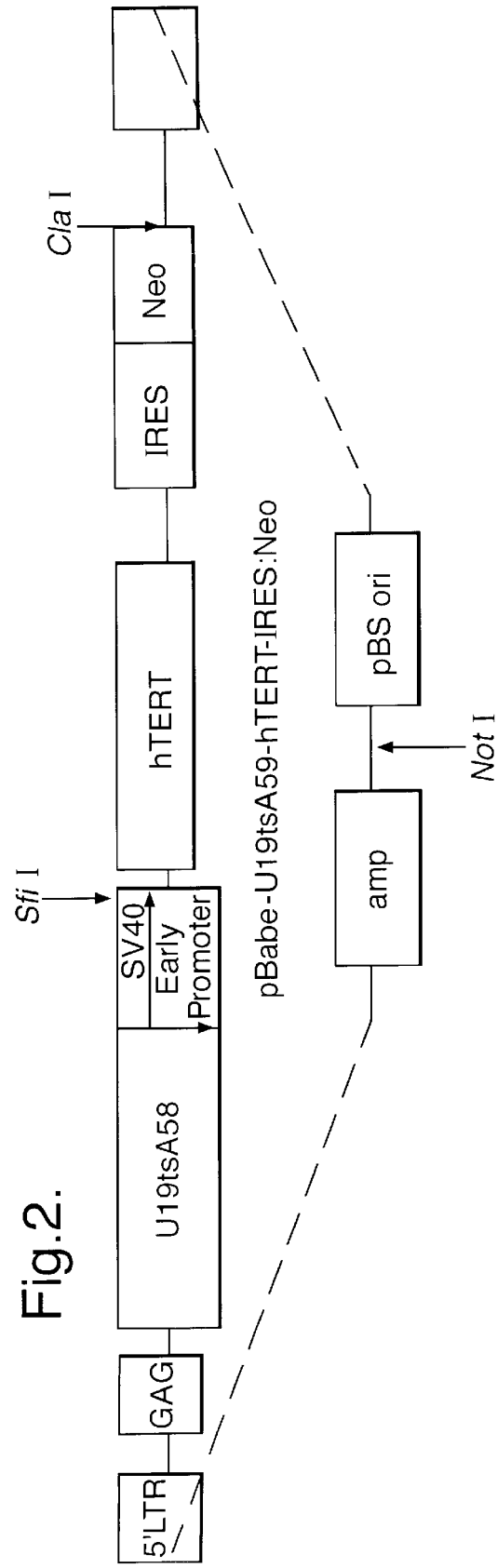
FIG. 2 is a schematic illustration of an alternative construct with the hTERT and oncogene in a different order from that in FIG. 1.

This construct is illustrated in FIG. 2. Mo MuLV LTR was used to drive U19tsA58, and the SV40 early promoter is used to drive hTERT and Neo. An IRES sequence was inserted between hTERT and Neo.

Cloning Strategy

Each vector was assembled in three sections. The vectors pBabe Neo-hTERT (hTERT excised from pCI-Neo-hTERT, provided by R. A. Weinberg, Whitehead Institute), and pBabe-Neo-U19tsA58 (where U19tsA58 is inserted in the sense orientation in respect to retrovirus transcription) were used to prepare the front-end of constructs 1 and 2, respectively.

The cloning of the IRES and its fusion in frame to the Neo gene was performed in the cloning vector pPolyIII-I (obtained from D. Kioussis, MRC, Mill Hill). pPolyIII-I is a useful vector for constructing gene sequences as it contains a large polylinker comprising many sites for restriction enzymes recognising a 6 nucleotide sequence. The third component was cloned from the vector pBabe Puro (pBabe with a puromycin resistance gene).

Construct 1

A. Cloning of IRES:Neo

The Neo sequence was amplified by PCR from the pLXSN (Clontech) vector. To keep the total length of the construct to a minimum, only the Neo coding region (2066 bp–2860 bp of pLXSN) was used. The 586 bp IRES (encephalomyocarditis virus (EMC) RNA 5' non-coding region) is available from the Novogen vector pCITE-1. The initiation region of EMC has a Bal I cloning site at position 2918 and an Nco I site at 2925 of pCITE-l, which can be used to insert the foreign sequence in frame.

It is recommended that foreign sequences lacking their own AUG are fused in frame to the viral AUG at 2915–2917, however cutting with Bal I produces a G at the beginning of the first codon after the AUG of the foreign sequence. This is incompatible with the Neo sequence where the first base after the AUG is A. To overcome this problem, the 5' Neo primer used to amplify the Neo sequence from pLXSN, was designed to recreate the IRES sequence between bases 2918 and 2929.

Forward Neo primer (SEQ ID NO. 1)

```
5' ...CC ACA ACC ATG ATT GAA CAA GAT G ...3'
       3' IRES          5'Neosequence
       sequence
```

To insert the 3' end of the Neo sequence into pPolyIII-I, the 3' PCR primer was designed to include a Sal I site and a Cla I site (for cloning from pPolyIII-I into pBabe).

Reverse Neo primer (SEQ ID NO. 2)

```
5' ...CCG TCG ACA TCG ATT CAG AAG AAC TCG TCA AG ...3'
         Sal I
              Cla I
                   3' neo sequence
```

It was therefore possible to cut the IRES from pCITE-1 with Eco RI and Bal I (isoschizomers are Mls I, Msc I) and ligate the sequence into the Eco RI and Bal I sites of pPolyIII-I. The Neo sequence was then amplified from the vector pLXSN using the previously mentioned forward and reverse Neo primers and the 3' region of the PCR product cut with Sal I prior to ligation into the Bal I and Sal I sites of pPolyIII-I-IRES.

B. Insertion of U19tsA58

U19tsA58 was excised from pZip-U19tsA58, (provided by P. Jat of Ludwig Institute for Cancer Research) by a Bam HI digest and inserted into the Bam HI site of pPolyIII-I-IRES:Neo in the sense orientation in respect to retrovirus transcription.

C. Final construct

The final construct was created by the three part ligation of:

(i) U19tsA58-IRES-Neo excised from pPolyIII-I-U19tsA58-IRES:Neo by Sfi I Cla I digest;

(ii) the front of the construct provided from the vector pBabe-Neo-hTERT, by digestion with Sfi I and Not I. Left hand section required; and (iii) pBS ori-containing fragment, acquired from the vector pBabe-Puro, by digestion with Cla I and Not I. Right hand side of vector required.

The final construct is as shown in FIG. 1.

Construct 2

A. pPolyIII-I-hTERT-IRES:Neo

To clone the hTERT cDNA and IRES:Neo into pPolyIII-I, pBabe Neo-hTERT was digested initially with Sal I, which cuts at the 3' end of hTERT. The cloning sites of hTERT are Eco RI (5') and Sal I (3'), however hTERT cannot be cloned into the Sal I site of pPolyIII-I as this is the cloning site for the 3' end of IRES:Neo. Therefore the hTERT sequence was first blunt-ended prior to excision of the cDNA sequence from pBabe Neo-hTERT with Eco RI. pPolyIII-I-IRES:Neo was cut with Eco RI, blunted and cut with Sal I to excise the IRES:Neo. hTERT and IRES:Neo were then cloned into the Eco RI and Sal I sites of pPolyIII-I joining at a blunt end ligation between 3' hTERT and 5' IRES:Neo.

The assembly of construct 2 involved a three part ligation of:

(i) hTERT-IRES:Neo excised from pPolyIII-I-IRES:Neo at the Sfi I and Cla I sites;

(ii) the left-hand side of construct 2, acquired from the vector pBabe-Neo-U19tsA58, by digestion with Sfi I and Not I; and (iii) the right-hand side of construct 2, acquired from the vector pBabe-Puro by digestion with Cla I and Not I.

The final construct is as shown in FIG. 2.

With regard to the design of the constructs, it may be more desirable to regulate expression of both the oncogene and hTERT components from the CMV promoter. This could be done by linking the components using an IRES sequence with insertion downstream of a CMV promoter, in a retroviral vector.

The constructs may be used to transduce suitable cells to produce conditionally-immortalised cells that have improved stability during passaging.

The recombinant cells of the invention may have use in therapy. Methods for the preparation of formulations for delivery to a patient will be apparent to the skilled person. Suitable excipients, diluents etc, will again be apparent based on current practice in preparing cell-based therapies. The amount of cells required for delivery will vary depending on the form of treatment, the severity of the disease/damage, and the need for applying multiple doses over a treatment period. However, the skilled person can readily determine the appropriate treatment based on existing cell transplantation therapies.

I claim:

1. A mammalian cell comprising a conditionally-inducible oncogene and an exogenous polynucleotide encoding the catalytic sub-unit of the telomerase complex.

2. The cell, according to claim 1, wherein the oncogene and the exogenous polynucleotide are in a recombinant vector.

3. The cell, according to claim 1, wherein the oncogene is temperature-sensitive.

4. The cell, according to claim 1, which is a human somatic cell.

5. The cell, according to claim 1, which is a mammalian stromal fibroblast cell or a mammalian microvascular cell.

6. The cell, according to claim 1, which is a human stem cell.

7. The cell, according to claim 6, which is a neuroepithelial stem cell.

8. The cell, according to claim 1, wherein the oncogene comprises a temperature-sensitive mutant of the SV-40 T-antigen gene.

9. The cell, according to claim 8, wherein the mutant is tsA58-U19.

10. A recombinant polynucleotide that encodes the catalytic sub-unit of the telomerase complex and a conditionally-inducible oncogene.

11. The polynucleotide, according to claim 10, further comprising a selectable marker gene and a promoter region.

12. A method for immortalising a mammalian cell, comprising incorporating within a proliferating cell a conditionally-inducible oncogene and an exogenous polynucleotide encoding the catalytic sub-unit of the telomerase complex.

13. The method, according to claim 12, wherein the oncogene and exogenous polynucleotide are incorporated into the cell within the first 10 cell divisions.

14. The method, according to claim 12, wherein the exogenous polynucleotide is introduced into the cell before the oncogene.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Forward 5' Neo primer.
<221> NAME/KEY: misc_feature
<222> LOCATION: (9)..(24)
<223> OTHER INFORMATION: Forward 5' Neo primer.

<400> SEQUENCE: 1
ccacaaccat gattgaacaa gatg                                             24

<210> SEQ ID NO 2
<211> LENGTH: 32
<212> TYPE: DNA
<213> ORGANISM: Artificial Sequence
<220> FEATURE:
<223> OTHER INFORMATION: Reverse 3' Neo primer.
<221> NAME/KEY: misc_feature
<222> LOCATION: (16)..(32)
<223> OTHER INFORMATION: Reverse 3' Neo primer.

<400> SEQUENCE: 2
ccgtcgacat cgattcagaa gaactcgtca ag                                    32